(12) United States Patent
Halle et al.

(10) Patent No.: US 6,303,308 B1
(45) Date of Patent: Oct. 16, 2001

(54) CLONING VECTORS AND THEIR PREPARATION AND USE FOR MRNA EXPRESSION PATTERN ANALYSIS

(75) Inventors: Jörn-Peter Halle, Penzberg; Johannes Regenbogen, Martinsried; Andreas Goppelt, München, all of (DE)

(73) Assignee: Switch Biotech AG, Martinsried (DE)

( * ) Notice: Subject to any disclaimer, the term of this patent is extended or adjusted under 35 U.S.C. 154(b) by 0 days.

(21) Appl. No.: 09/307,924

(22) Filed: May 10, 1999

(30) Foreign Application Priority Data

May 18, 1998 (DE) .............................................. 198 22 287

(51) Int. Cl.⁷ .............................. C12Q 1/68; C12P 19/34; C07H 21/04
(52) U.S. Cl. ........................... 435/6; 435/91.1; 435/91.3; 536/24.33
(58) Field of Search ............................. 435/6, 91.1, 91.3; 536/24.33

(56) References Cited

U.S. PATENT DOCUMENTS

| 5,459,037 | 10/1995 | Sutcliffe et al. | 435/6 |
|---|---|---|---|
| 5,627,369 | 5/1997 | Vestal et al. | 250/287 |
| 5,681,726 | 10/1997 | Huse et al. | 435/91.52 |
| 5,691,141 | 11/1997 | Köster | 435/6 |
| 5,695,937 | 12/1997 | Kinzler et al. | 435/6 |
| 5,712,126 | 1/1998 | Weissman et al. | 435/91.2 |
| 5,714,330 | 2/1998 | Brenner et al. | 435/6 |
| 5,716,825 | 2/1998 | Hancock et al. | 435/286.5 |
| 6,080,540 * | 1/2000 | Wigler et al. | 435/6 |

OTHER PUBLICATIONS

New England Biolabs Catalog, "pnEB 193", pp. 214–215, 1996.*
Adams et al., "Complementary DNA Sequencing: Expressed Sequence Tags and Human Genome Project," Science 252:1651–1656 (1991).
Adams et al., "Sequence Identification of 2,375 Human Brain Genes," Nature 355:632–634 (1992).
Akopian and Wood, "Peripheral Nervous System–Specific Genes Identified by Subtractive cDNA Cloning," J. Biol. Chem. 270:21264–21270 (1995).
Brenner and Livak, "DNA Fingerprinting by Sampled Sequencing," Proc. Natl. Acad. Sci. USA 86:8902–8906 (1989).
Carrano et al., "A High–Resolution, Fluorescence–Based, Semiautomated Method for DNA Fingerprinting," Genomics 4:129–136 (1989).
Chollet and Kawashima, "Biotin–Labeled Synthetic Oligodeoxyribonucleotides: Chemical Synthesis and Uses as Hybridization Probes," Nucleic Acids Res. 13:1529–1541 (1985).
Cozzarelli et al., "Enzymic Synthesis of DNA," J. Mol. Biol. 45:513–531 (1969).

Deleersnijder et al., "Isolation of Markers for Chondro–osteogenic Differentiation Using cDNA Library Subtraction," J. Biol. Chem. 271:19475–19482 (1996).
Diatchenko et al., "Suppression Subtractive Hybridization: A Method for Generating Differentially Regulated or Tissue–Specific cDNA Probes and Libraries," Proc. Natl. Acad. Sci. USA 93:6025–6030 (1996).
Francois et al., "Sequence–Specific Recognition of the Major Groove of DNA by Oligodeoxynucleotides Via Triple Helix Formation. Footprinting Studies," Nucleic Acids Res. 16:11431–11440 (1988).
Frank and Köster, "DNA Chain Length Markers and the Influence of Base Composition on Electrophoretic Mobility of Oligodeoxyribonucleotides in Polyacrylamide–Gels," Nucleic Acids Res. 6:2069–2087 (1979).
Fu et al., "Sequencing Exons 5 to 8 of the p53 Gene by MALDI–TOF Mass Spectrometry," Nature Biotech. 16:381–384 (1998).
Gurskaya et al., "Equalizing cDNA Subtraction Based on Selective Suppression of Polymerase Chain Reaction: Cloning of Jurkat Cell Transcripts Induced by Phytohemaglutinin and Phorbol 12–Myristate 13–Acetate," Anal. Biochem. 240:90–97 (1996).
Hubank and Schatz, "Identifying Differences in mRNA Expression by Representational Difference Analysis of cDNA," Nucleic Acids Res. 22:5640–5648 (1994).
Instructions for the "cDNA Synthesis Kit," Strategene GmbH, Heidelberg, pp. 1–52 (1998).
Khan et al., "Efficient Double Stranded Sequencing of cDNA Clones Containing Long Poly(A) Tails Using Anchored Poly(dT) Primers," Nucleic Acids Res. 19:1715 (1991).
Liang and Pardee, "Differential Display of Eukaryotic Messenger RNA by Means of the Polymerase Chain Reaction," Science 257:967–971 (1992).
Liang et al., "Differential Display and Cloning of Messenger RNAs from Human Breast Cancer versus Mammary Epithelial Cells," Cancer Res. 52:6966–6968 (1992).
Lisitsyn and Wigler, "Cloning the Differences Between Two Complex Genomes," Science 259:946–951 (1993).
Maxam and Gilbert, "A New Method for Sequencing DNA," Proc. Natl. Acad. Sci. USA 74:560–564 (1977).

(List continued on next page.)

*Primary Examiner*—W. Gary Jones
*Assistant Examiner*—Arun Kr. Chakrabarti
(74) *Attorney, Agent, or Firm*—Clark & Elbing LLP

(57) ABSTRACT

Disclosed herein are cloning vectors which include:

(a) a cloning site which permits the cloning of a nucleic acid in defined orientation;

(b) at least one cleavage site adjacent to the cloning site, the cleavage site being rarely-occurring in nucleic acids; and (c) a long region which is located on the side of the cloning site opposite to the cleavage site (b), wherein the long region and the region between the cloning site and the cleavage site (b) contain neither the cloning site nor at least two frequently-occurring cleavage sites.

21 Claims, 4 Drawing Sheets

OTHER PUBLICATIONS

Prashar and Weissman, "Analysis of Differential Gene Expression by Display of 3' End Restriction Fragments of cDNAs," Proc. Natl. Acad. Sci. USA 93:659–663 (1996).

Roychoudhury et al., "Terminal Labeling and Addition of Homopolymer Tracts to Duplex DNA Fragments by Terminal Deoxynucleotidyl Transferase," Nucleic Acids Res. 3:863–877 (1976).

Sambrook et al., Molecular Cloning: A Laboratory Manual, Cold Spring Harbor, Cold Spring Harbor Laboratory Press, New York, pp. 1.25–1.31, 1.52–1.84, 5.28–5.37, 6.30–6.31, 7.22–7.29, 8.11–8.31, and 11.45–11.47.

Sellem et al., "Differential Expression of Albumin and α–Fetoprotein Genes in Fetal Tissues of Mouse and Rat," Dev. Biol. 102:51–60 (1984).

Sun et al., "Oligonucleotide Directed Triple Helix Formation," Curr. Opin. Struct. Biol. 6:327–333 (1996).

Tu and Cohen, "3'–End Labeling of DNA With [α–$^{32}$P] Cordycepin–5'–Triphosphate," Gene 10:177–183 (1980).

Velculescu et al., "Serial Analysis of Gene Expression," Science 270:484–487 (1995).

Velculescu et al., "Characterization of the Yeast Transcriptome," Cell 88:243–251 (1997).

White et al., "Recognition of the Four Watson–Crick Base Pairs in the DNA Minor Groove by Synthetic Ligands," Nature 391:468–471 (1998).

Yang and Sytkowski, "Cloning Differentially Expressed Genes by Linker Capture Subtraction," Anal. Biochem. 237:109–114 (1996).

Yanisch–Perron et al., "Improved M13 Phage Cloning Vectors and Host Strains: Nucleotide Sequences of the M13mp18 and pUC19 Vectors," Gene 33:103–119 (1985).

Zeng et al., "Differential cDNA Cloning by Enzymatic Degrading Subtraction (EDS)," Nucleic Acids Res. 22:4381–4385 (1994).

Zhang et al., "Gene Expression Profiles in Normal and Cancer Cells," Science 276:1268–1272 (1997).

* cited by examiner

CLONING VECTORS AND THEIR PREPARATION AND USE FOR MRNA EXPRESSION PATTERN ANALYSIS

CROSS REFERENCE TO RELATED APPLICATIONS

This application claims priority from German Patent Application 19822287.4, filed May 18, 1998.

BACKGROUND OF THE INVENTION

In general, the invention features a cloning vector useful, for example, for mRNA expression pattern analysis.

Messenger RNA expression pattern comparison between different cells or tissues is becoming increasingly important in biomedical research. For example, conclusions about errors in gene regulation can be made from a comparison between healthy and diseased tissue. In addition, comparisons between pharmaceutically-treated and untreated tissues, cells, or control animals permit conclusions to be drawn about the mechanisms of action of pharmaceuticals. Comparisons between different tissues or cell types also permit the identification of differentiation or control genes.

Various methods have been developed for representing mRNA expression patterns, but all generally possess certain disadvantages. For example, methods based on subtractive cDNA libraries typically detect only large differences in expression patterns. Techniques based on differential display RT-PCR (and further developments thereof) are able to analyze only a restricted subset of all genes and are generally very time-consuming and error-prone.

The expressed sequence tag (EST) approach analyzes expression patterns by sequencing many clones from cDNA libraries. Even short sequences of 3' cDNA ends (that is, marker or "tag" sequences) may be used to unambiguously identify a gene. In addition, different frequencies of cDNAs in different libraries permit conclusions to be drawn about changes in gene expression. Although this approach provides very accurate quantitative information, it is very labor-intensive. Further developments of this method have concentrated primarily on increasing the throughput by means of serial or parallel sequencing of many short markers.

A number of techniques for gene expression analysis have been described. For example, U.S. Pat. No. 5,695,937 describes serial analysis of gene expression (SAGE) in which short cDNA sequences are first prepared from mRNAs. They are then dimerized and multimerized and, after cloning, manually sequenced. The disadvantage of this method is that only a small part (<20 bp) of the cDNA may generally be cloned and identified by sequencing.

Another technique is described in U.S. Pat. No. 5,459,037. This patent describes a method for simultaneous sequence-specific identification of mRNAs in an mRNA population in which a primer mixture is used to synthesize corresponding cDNAs. The cDNAs are in turn transcribed into cRNAs with the aid of RNA polymerases, and PCR amplification is then carried out. The expression pattern is analyzed by comparing the intensities of the bands. The disadvantage of this method is that the PCR step frequently gives erroneous results.

U.S. Pat. No. 5,712,126 describes the selective PCR amplification of the 3' ends of cDNA fragments. This technique does not use a primer mixture, but 12 different cDNA syntheses are carried out, and thus there is corresponding additional complexity. Moreover, the expression patterns are analyzed by comparing the intensities of the bands, with a corresponding range of error.

Another problem in the analysis of gene expression patterns is that cDNA libraries generally contain a high percentage of clones containing only incomplete or no cDNAs. These reduce the analysis throughput and may falsify the results of the analysis.

SUMMARY OF THE INVENTION

The present invention provides a method which avoids the disadvantages described above. In particular, this invention features cloning vectors and methods for their use which make it possible to dispense with an additional step of cDNA sequencing, facilitating a cost-effective and high throughput analysis. In addition, this technique makes it possible to also dispense with the use of the polymerase chain reaction (PCR), again providing an advantage because a PCR step frequently leads to defective results.

In particular, the present invention features a cloning vector which includes:
(a) a cloning site which permits the cloning of a nucleic acid in a defined orientation,
(b) at least one cleavage site adjacent to the cloning site (a) and only rarely-present in nucleic acids,
(c) a long region which is located on the side of the cloning site (a) opposite to the cleavage site (b), where the long region and the region between the cloning site (a) and the cleavage site (b) contains neither the cloning site nor at least two cleavage sites which frequently occur in nucleic acids.

In a preferred embodiment, the long region is longer than the fragments obtainable by cutting with restriction nucleases which recognize the frequently-occurring cleavage sites.

In another preferred embodiment, the cloning vector contains on the other side of the cloning site a short region with several different cleavage sites which are frequently-occurring in nucleic acids but which are not present in the long region.

In yet another preferred embodiment, the cloning site contains two different cleavage sites. One example of a cloning vector according to the invention is depicted in FIG. 2.

According to the present invention, a cleavage site which is "frequently-occurring" in nucleic acids means a site which is recognized by restriction endonucleases, also called restriction enzymes, having a recognition sequence of not more than 4 nucleotides.

Examples of restriction endonucleases of this type include, without limitation, AciI, AluI, BfaI, BsaJI, BslI, BscFI, BssKI, BstUI, Cac8I, CfoI, Csp6I, CviJI, DdeI, DpnI, DpnII, FmuI, Fnu4HI, HaeIII, HhaI, HinfI, HinPI, HpaII, MaeII, MaeIII, MboI, MnlI, MseI, MspI, MwoI, NlaIII, NlaIV, RsaI, Sau3AI, Sau96I, ScrFI, TaiI, TaqI, Tsp4CI, and Tsp509I, all of which are obtainable.

A cloning site and cleavage site which is only "rarely-occurring" in nucleic acids means, according to the present invention, independently of one another, a site which is recognized by restriction endonucleases with a recognition sequence of not less than 5 nucleotides, and preferably not less than 6 nucleotides, and which may contain rarely-occurring nucleotide combinations such as CG. This term also includes sites recognized by restriction endonucleases with a recognition sequence of not less than 8 nucleotides.

Examples of restriction endonucleases having one or more recognition sites of 5 nucleotides include, without limitation, AclWI, Alw26I, AlwI, AsuHPI, AvaII, BbvI, BccI, BcefI, BinI, BsbI, BscGI, Bse1I, BseNI, BsmAI, BsmFI, BspLU11III, BsrI, BsrSI, Bst71I, BstF5I, BstNI, CjeI, CjePI, EcoRII, FauI, FinI, FokI, HgaI, HphI, MboII, NciI, PleI, SfaNI, SimI, TauI, TfiI, TseI, Tsp45I, TspRI, and Vpa11AI, all of which are obtainable.

Examples of restriction endonucleases having at least one recognition sequence of 6 nucleotides include, without limitation, AccI, AflIII, ApoI, AvaI, BanI, BanII, BmgI, BsaI, BsaHI, BsaWI, BsiEI, BsiHKAI, BsoBI, Bsp1286I, BsrFI, BstYI, DsaI, EaeI, EcoO109I, GdiII, HaeI, HaeII, Hin4I, HincII, MmeI, MslI, MspA1I, NspI, SfcI, StyI, TatI, Tth111II, AatI, Acc113I, Acc65I, AcINI, AflIII, Alw44I, ApaI, ApaLI, AseI, Asp718I, AvrII, BalI, BamHI, BbuI, BbsI, BclI, BfrI, BglI, BglII, BlnI, BpiI, BpmI, BsaI, BsaMI, BseRI, BsmBI, BsmI, Bsp120I, Bsp1407I, Bsp19I, BspHI, BspLU11I, BspMI, BspTI, BsrGI, Bst1107I, Bst98I, DraI, Eam1104I, EarI, Ecl136II, Eco147I, Eco255I, Eco57I, EcoNI, EcoRI, EcoRV, EcoT22I, HindIII, HpaI, KpnI, MfeI, MscI, NcoI, NdeI, NheI, NsiI, PstI, PvuII, SacI, ScaI, SpeI, SphI, SspI, SstI, StuI, and XbaI.

Examples of restriction endonucleases which recognize a recognition sequence of 6 nucleotides which contain rarely-occurring nucleotide combinations such as CG include, without limitation, AatII, BbeI, BsiI, BsiWI, BsmBI, BspDI, BsrBI, BssHII, Bst2BI, BstBI, ClaI, EagI, EciI, Eco47III, EheI, Esp3I, FspI, KasI, MluI, NarI, NruI, Pfl1108I, PmlI, Psp1406I, PvuI, SacII, SalI, SnaBI, and XhoI.

And examples of restriction endonucleases which recognize a recognition sequence larger than 6 nucleotides include, without limitation, AscI, BaeI, FseI, NotI, PacI, PmeI, PpuMI, RsrII, SanDI, SapI, SexAI, SfiI, SgfI, SgrAI, SrfI, Sse8387I, SwaI, I-CeuI, PI-PspI, I-PpoI, PI-TliI, and PI-SceI.

The cloning vector according to the invention is used, for example, to identify a cDNA clone on the basis of the characteristic distance of restriction cleavage sites from the 3' end of the cDNA (see, for example, FIG. 1). Since this distance may be identical for a given restriction enzyme in different genes, unambiguous identification is possible by analysis of the DNA fragment lengths or DNA masses of the 3' ends of the cDNAs which are generated by at least two different restriction enzymes. The fragments of the cDNA which are labeled in the method preferably comprise parts of the 3' poly-A tail, the cDNA up to the next restriction cleavage site in the 5' direction, and short vector sequences (see FIG. 1)

For this reason, the "long region," according to the invention, is preferably longer than the fragments obtainable by cutting cDNAs with restriction endonucleases which recognize cleavage sites frequently-occurring in nucleic acids. In particular, the long region is longer than about 500 nucleotides, and preferably longer than about 1000 nucleotides. The "short region," according to a further embodiment of the present invention, is preferably smaller than the length of the nucleic acid which extends from cleavage site (b) to the first possible frequently-occurring cleavage site in the nucleic acid to be cloned into the vector, or smaller than the length of the nucleic acid which extends from cleavage site (b) to, preferably, the start of the poly(A) tail of the cDNA to be cloned into the vector. In particular, the short region is smaller than about 100 nucleotides, and preferably smaller than about 30 nucleotides.

An alternative possibility is for the short region to be omitted if, as in the example of the present invention (FIG. 1), the choice of the recognition site E3 ensures that only the E3-E5 (or E3-E4 and E3-E6) fragments which contain the 3' end of the cDNA are labeled, but not the corresponding fragments of the vector.

A particularly preferred vector according to the invention generally has the following properties (see also FIG. 2):

(1) It contains an insertion site for the cDNA having the recognition sites of the restriction enzymes E1 and E2 which make directed cloning of the cDNA possible. The recognition sites for the enzymes E1 and E2 generally occur only once in the vector. The cloned cDNAs all have the same orientation in the vector. The recognition sequence E2 is located at the 5' end of the cDNA, and the recognition sequence E1 is located at the 3' end of the cDNA.

(2) A recognition site for a restriction enzyme (E3) which cuts rarely is located immediately beside the cloning site at the 3' end of the cDNA (E1). An alternative possibility is for the 3' cloning site E1 itself to be recognized by such an enzyme. The recognition site E3 generally occurs only once in the vector. It serves to allow the vector to be digested and labeled in a defined manner without cutting the cDNA.

(3) At least two recognition sites for restriction enzymes which cut the cDNA frequently (region B, recognition sites E4, E5, and E6) are located within a short distance (less than the distance from cleavage site E3 to the first non-A nucleotide at the 3' end of the cDNA, and preferably less than 30 base pairs). These sites serve to allow the cDNA to be cut in a defined manner without simultaneous production of another labeled fragment of comparable size. In the example shown in FIG. 3, all of the E3-E5 fragments which contain the 3' cDNA end are larger than the E3-E5 fragment of the vector. The same applies to the E3-E4 and E3-E6 fragments.

(4) Immediately following the 5' cloning site there is a long region (region A) which preferably has a length of more than 1000 nucleotides and contains no recognition sites for the restriction enzymes described previously (enzymes E1, E2, E3, E4, E5, and E6). This region confers a minimum size on labeled fragments derived from empty vectors (without cDNA insert) or vectors with incomplete or short cDNA inserts (without recognition sites for restriction enzymes E3, E4, E5). This minimum size essentially prevents the fragments from being detected in the range of, preferably, 30 to 1000 base pairs (see FIG. 4). The labeled fragments of most genes can be detected in this range.

(5) The vector contains a selection marker and an origin of replication.

Vectors according to the invention can be prepared by standard cloning methods. One possibility for vector preparation is described in Example 1. The present invention therefore also relates to the preparation of the vector by combining the individual vector components and, in particular, by combining the individual components by genetic manipulation.

The essential advantages of the present cloning vectors are that specific labeling of the 3' end of a cDNA is made possible, and, moreover, that the assignment to one gene is unambiguous even if many, for example, up to about 200, cDNA clones are analyzed simultaneously. This makes very rapid analysis of gene expression possible.

The present invention therefore also relates to a method for identifying a nucleic acid which includes the following steps:

(1) cloning a nucleic acid which is present where appropriate in a nucleic acid population into a cloning vector according to the invention, with the orientation of the nucleic acid in the cloning vector being fixed;

(2) hydrolyzing with a restriction endonuclease which recognizes rarely-occurring nucleic acid cleavage sites;

(3) dividing the reaction mixture obtained in step (2) into several portions;

(4) where appropriate, labeling one or both ends of the nucleic acid portioned in step (3);

(5) hydrolyzing one portion with a restriction endonuclease which recognizes frequently-occurring nucleic acid cleavage sites;

(6) hydrolyzing another portion with another restriction endonuclease which recognizes frequently-occurring nucleic acid cleavage sites;

(7) fractionating the portioned nucleic acids; and (8) analyzing the fractionated nucleic acids.

The method generally begins with cDNA synthesis, using standard protocols, starting from mRNA which has been obtained, for example, from cells or tissue. It is moreover ensured, for example, by the choice of a primer mixture and the conditions for synthesizing the first strand, that the cDNA synthesis starts at a fixed position at the 3' end of the mRNA. After this step, the cDNAs are inserted in identical orientation into a cloning vector according to the invention (see, for example, FIG. 2).

As already mentioned above, the cloning vector makes it possible for the 3' end of the cDNA to be specifically labeled. A particularly preferred vector additionally harbors, on both sites of the insertion site, defined regions which carry out two tasks. In particular, the vector contains:

(i) a short region, which is located for example at the 3' end of the cDNA, that ensures that labeled fragments of the vector are so small (for example, <30 base pairs) that they do not interfere with the analysis of the fragments of the 3' end of the cDNA which are larger than, for example, 30 base pairs; and (ii) a long region, which is located for example at the 5' end of the cDNA, that ensures that very short cDNAs which harbor no restriction enzyme cleavage sites (and which would thus not produce defined fragment lengths of the 3' region) generate labeled fragments which are in turn too large (for example, >1000 bp) to be detected in the method according to the invention. This results in a so-called detection window from, for example, 30 to more than 1000 base pairs, in which the 3' fragments of most cDNAs can be detected.

After insertion of the cDNAs into the cloning vector, the vectors are replicated after transformation into suitable cells, for example, prokaryotic cells such as *E. coli*. This results in so-called cDNA libraries which reflect the expression pattern of the mRNAs.

The cDNA clones are identified after preparation, labeling, and analysis of the 3' ends by comparison with a database which contains the fragment lengths or fragment masses of the restriction fragments of the 3' region of known cDNAs. This identification is possible even if mixtures of up to about 200 cDNA clones are analyzed simultaneously.

In addition, comparison with the database of known genes allows unknown genes in the cDNA populations or mixtures to be identified, cloned, and in turn integrated into the database. It is thus also possible by this method to construct specific novel gene banks which are characterized by the expression pattern of the mRNAs on which they are based.

An essential advantage of the method according to the invention is that very many cDNA clones can be rapidly identified, for example, up to 50,000 clones per worker per week, which makes it possible to determine the relative frequency of virtually all genes in a cDNA library and thus a comprehensive expression pattern of the cells or of the tissue from which the mRNAs have been obtained. Comparison of different cDNA libraries makes it possible to identify differentially expressed genes easily and rapidly.

The method according to the invention is also advantageous because clones which contain only incomplete or no cDNAs are excluded from the analysis.

In a preferred embodiment, the reaction mixture obtained in step (2) above is divided into at least two, and preferably three, portions and the individual portions of nucleic acids are preferably differentially labeled. In a further step it is also possible, in the case of differential labeling, for the individual portions of nucleic acids to be combined again before the fractionation in step (7).

Analysis of the nucleic acids fractionated in step (7) normally takes place via their size and/or mass, and it is possible in a step (8) to compare the size and/or mass of the fractionated nucleic acids with the size and/or mass of known nucleic acids.

The coding nucleic acid in the method according to the invention is generally a so-called cDNA, which can be prepared as follows:

(a) hybridization of a mixture of various primers of the formula (I):

$$5' \text{ Cleavage site I-}(T)_n\text{-V } 3' \qquad (I),$$

where cleavage site I is a cleavage site of a restriction enzyme I; T is thymidine; n is an integer from about 5–50, preferably about 7–40, more preferably about 7–30, even more preferably about 10–20, and most preferably about 15–20; V is A (adenine), G (guanine), or C (cytosine); and the primer mixture contains all the permutations of V, in one or more mRNAs;

(b) preparation of a double-stranded cDNA;

(c) where appropriate, attachment of linkers or adapters (that is, precut linkers) which contain a cleavage site for a restriction enzyme II, or overhangs (produced for example, using terminal transferase) to the 5' and 3' ends of the double-stranded cDNA;

(d) hydrolysis of the double-stranded cDNA with the restriction enzyme I and, where appropriate, the restriction enzyme II.

Possible examples of overhangs are poly(A), poly(T), poly(G), or poly(C) sequences.

In a preferred embodiment, the primer mixture contains primers of the formula (II):

$$5' \text{ cleavage site I-}(T)_n\text{-VN } 3' \qquad (II),$$

with N being A, G, C, or T, and where the primer mixture contains all permutations of V and N.

The double-stranded cDNA hydrolyzed in step (d) is then preferably cloned into a cloning vector according to the invention having the cleavage sites of the restriction enzymes I and II.

The present invention therefore further relates to the use of the cloning vectors according to the invention for identifying genes and to gene banks obtainable by a method according to the invention, with such gene banks being useful for identifying genes which can subsequently be characterized, for example, by sequencing.

The following general example describes the method according to the invention in more detail, to illustrate the individual embodiments, as well as its advantages and possible uses.

Purification of mRNA from Tissue or Cells

RNA is normally extracted from, for example, tissues or cells and purified by standard methods (see, for example, Molecular Cloning: A Laboratory Manual, Cold Spring Harbor, Cold Spring Harbor Laboratory Press, New York, Chapter 7). The RNA is preferably isolated in the presence of denaturing agents such as guanidinium chloride or guanidinium thiocyanate. It is also possible alternatively to use other detergents and extractants.

The extraction of the complete RNA is generally followed by isolation of the mRNA. The mRNA is purified by known methods using, for example, oligo-dT-cellulose or other chromatography materials able to bind the polyadenylated part of the mRNA (supra, Chapter 7). Alternatively, the mRNA isolation can be omitted, and the method can be carried out with the complete RNA, or the mRNA can be isolated directly from the tissue without previously purifying the complete RNA (for example using the "Oligotex direct mRNA Isolation Kit," Qiagen GmbH, Hilden, Germany).

cDNA Synthesis with an Anchored Primer

Synthesis of the cDNA first strand is generally carried out with a mixture of primers which recognize the poly-A tail of the mRNA and at least one other base of the mRNA (so-called anchored primers). This makes it possible to start the synthesis of the cDNA exactly at the junction of the mRNA sequence with the poly-A tail, whereby the 3' end of the cDNA is fixed.

The anchored primers preferably each consist of:

(i) a poly-T region of about 5–50, preferably about 7–40, more preferably about 7–30, even more preferably about 10–20, and most preferably about 15–20 thymidine (T) residues, which recognizes the poly-A tail of the mRNAs;

(ii) a recognition site for a restriction enzyme 5' of the poly-T region, which site is used for the subsequent cloning;

(iii) preferably, an extension of the 5' region with a nonspecific sequence which improves the efficiency of the hydrolysis at the recognition site by the appropriate restriction enzyme;

(iv) one of the bases A, G, or C directly connected 3' to the poly-T region, which recognizes the mRNA and anchors the 3' end of the cDNA. (Use of a mixture of all three primers characterized by the bases A, G, and C makes it possible to recognize any particular mRNA in the mRNA population); and (v) where appropriate, another nucleotide selected from the bases, A, G, C, or T, connected 3' to the base mentioned under (iv), which nucleotide recognizes the mRNA and improves the specific start of the cDNA synthesis. (Use of a mixture of all twelve primers characterized by the bases, A, G, C, and T means that any particular mRNA is recognized without the possibility of unwanted selection of the mRNAs.)

The primer can be represented, for example, by the following general formula (I):

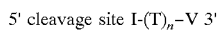

and preferably by the following general formula (II):

where cleavage site I is a cleavage site of a restriction enzyme I, n has the abovementioned meaning, V equals A, G, or C and, where appropriate, N equals A, G, C, or T, and the primer mixture contains all permutations of V and N.

A typical primer mixture with, for example, an XhoI cleavage site consisting of 12 different primers has the following formula (III), for example (SEQ ID NO: 1):

with V being A, G, or C, and N being A, G, C, or T.

The optimal conditions for the hybridization of the primer mixture to the mRNA which make it possible for cDNA synthesis to be both efficient and fixed at the 3' end are preferably determined experimentally for each primer mixture. For the primer mixture of formula (III), for example, these conditions are 5 μg of mRNA in 50 μl of hybridization buffer (50 mM Tris-HCl, pH8.3, 50 mM KCl, 3 mM MgCl$_2$) which contains 10 μM primer mixture, which are denatured at 67° C. for 5 minutes, and then hybridized at 38° C. for 30 minutes.

The double-stranded cDNA is generally synthesized by standard methods (see, for example, Sambrook et al., 1989, supra, Chapter 8). The cDNA is preferably synthesized using a reverse transcriptase and a dNTP mixture, it being possible for one of the deoxynucleotides to be methylated in order to make later breakdown of the synthesized strand difficult or impossible (see, for example, instructions for the "cDNA Synthesis Kit", Stratagene GmbH, Heidelberg, Germany; U.S. Pat. No. 5,681,726).

Cleavage of the cDNA with Restriction Enzymes

The cloned cDNA is generally cut with the restriction enzyme (restriction enzyme I) which recognizes the 5' end of the primer mixture used for the cDNA synthesis (for example, XhoI). The cDNA is generally additionally cleaved with a second enzyme of a different type (restriction enzyme II).

An alternative possibility is to ligate a precut adapter, for example, an EcoRI adapter (see, for example, Sambrook et al, 1989, supra, Chapter 8, or instructions for the "cDNA Synthesis Kit," Stratagene GmbH, Heidelberg, Germany). The cDNA might furthermore also be hydrolyzed with an enzyme which cuts within the cDNA. The reaction conditions for the hydrolysis of DNAs with restriction endonucleases are generally known (see, for example, supra, Chapter 5).

Directed Cloning of the cDNA

The hydrolysis is followed by integration of the cut cDNA into an appropriately cut cloning vector according to the invention by standard methods (see, for example, supra, Chapter 1). The cloning is normally carried out using T4 DNA ligase or comparable enzymes.

Plating Out of the cDNA Library

The cloning vectors according to the invention in which the cDNAs have been integrated can be used, for example, to transform cells and generate a cDNA library. Suitable cells able to take up the vectors with high efficiency and suitable transformation and transfection methods are described, for example, in Sambrook et al., 1989, supra. Prokaryotic cells are normally used, preferably E. coli, for example, the E. coli strains SURE, XL 1-Blue MRF' or XL10-Gold (Stratagene GmbH, Heidelberg, Germany).

After the transformation, the concentration of the resistant cells is determined by plating out on selection medium and incubating under growth conditions. The cDNA bank is then plated out, for example, in such a way that there is growth either of a number of clones suitable for the labeling and detection on each plate (for example, 100 colonies/plate, see FIG. 5), or of a number suitable for manual or automatic picking of clones on each plate. In the second case, the colonies are transferred into liquid medium and incubated under growth conditions.

Mixing of cDNA Clones

A suitable number of clones (colonies) is either rinsed off the plate and combined, or an appropriate number of liquid cultures are combined.

DNA Plasmid Preparation

The plasmid DNA is isolated from the combined clones by standard methods and preferably purified so that the subsequent reactions can proceed without interference from contamination.

Hydrolysis with Restriction Enzyme

The DNA is distributed, for example, to at least two, preferably three, mixtures and cut with the restriction enzyme which is located at the 3' end of the cDNA and which cuts cDNAs only rarely (enzyme E3, see FIGS. 2, 3, 4, and 5).

Labeling of the DNA

The DNA ends which have been produced by hydrolysis with the enzyme E3 are specifically labeled, for example, with an isotope (stable or radioactive), a dye, or a ligand (for example, biotin or digoxigenin). Various methods are available for this labeling. These include:

(A) enzymatic labeling (see, for example, Sambrook et al., 1989, supra, Chapter 5), for example, by (i) ligation of a labeled oligonucleotide, (ii) kinase reaction with a labeled nucleotide triphosphate, (iii) DNA polymerase reaction with a labeled deoxynucleotide triphosphate (end-labeling, see, for example, Sambrook et al., 1989, supra, Chapter 10), or (iv) terminal transferase reaction with a labeled nucleotide triphosphate or deoxynucleotide triphosphate;

(B) chemical labeling, for example by 5' labeling via an aminohexyl-phosphoramide compound; and (C) hybridization of a labeled oligonucleotide, for example, by (i) annealing of a labeled oligonucleotide which has a sequence complementary to one strand of the DNA end, the annealing generally taking place by standard methods (for example, by a denaturation/hybridization cycle), or (ii) annealing of a labeled oligonucleotide which is able to form a triple helix with the DNA end.

Region B in the vector according to the invention can be omitted when using the labeling methods described below which label only the DNA end adjacent to the inserted cDNA. In this case, the vector fragment is not labeled. It therefore cannot be detected and thus does not interfere with the analysis. It is therefore also unnecessary to restrict its length, by using region B, to for example less than 30 base pairs. Suitable methods for specific labeling of one end are: (i) ligation of a labeled oligonucleotide, (ii) DNA polymerase reaction with a labeled deoxynucleotide triphosphate, or (iii) hybridization of a labeled oligonucleotide. These labeling reactions may take place unilaterally if the DNA ends produced by the hydrolysis with a restriction enzyme are not identical.

Examples of the specific unilateral labeling of the DNA ends include:

(i) Ligation of a labeled oligonucleotide. Hydrolysis with Sfi1 as enzyme E3 (recognition sequence: GGCCNNNNNGGCC) produces the following DNA ends (SEQ ID NO: 2):

```
5'-GGCCAGGGTGGCC-3'   ->  5'-GGCCAGGG   TGGCC-3'
3'-CCGGTCCCACCGG-5'       3'-CCGGT      CCCACCGG-5'
```

Ligation with a labeled, double-stranded oligonucleotide with a 3' overhang of three cytidines then results in labeling of only one DNA end:

```
5'-GGCCAGGG +   NNNNNNNNNNNN
3'-CCGGT    CCCNNNNNNNNNNNN-label
5'-GGCCAGGGNNNNNNNNNNN
3'-CCGGTCCCNNNNNNNNNNNN-label
``` with N equal to A, G, C, or T.

The other DNA end is not labeled because the overhang is incompatible.

```
5'-GGCCACCC +   NNNNNNNNNNNN
3'-CCGGT    CCCNNNNNNNNNNNN-label.
```

(ii) DNA polymerase reaction with a labeled deoxynucleotide triphosphate. A unilateral labeling by incorporation of labeled deoxynucleotides preferably takes place after the hydrolysis with enzymes E3 such as Rsr11 (recognition site CGGWCCG), which forms a 5' overhang.

```
5'-CGGACCG-3'  -> 5'-CG   GACCG-3'
3'-GCCTGGC-5'     3'-GCCTG   GC-5'.
```

Labeling of the one DNA end takes place by filling in the overhang with a DNA polymerase and labeled dATP in the presence of unlabelled dCTP, dGTP, and dTTP:

5'-CG<u>GAC</u>   (underlined   nucleotides:   polymerase incorporation, A: labeled).

3'-GCCTG.

The other DNA end is filled in but not labeled:

5'-CG<u>GTC</u>

3'-GCCAG.

(iii) Hybridization of a labeled oligonucleotide. Hydrolysis with Sf11 as enzyme E3 (recognition sequence: GGCCNNNNNGGCC) produces, for example, the following DNA ends (SEQ ID NOS: 3–5):

5'-CTCGAGGCCAGGGTGGCCGATCGA-3'→
3'-GAGCTCCGGTCCCACCGGCTAGCT-5'

```
5'-CTCGAGGCCAGGG   TGGCCGATCGA-3'.
3'-GAGCTCCGGT      CCCACCGGCTAGCT-5'.
```

The labeling takes place by hybridization with a labeled oligonucleotide which is complementary to only one DNA end (label 5'-CCCTGGCCTCGAG; SEQ ID NO: 6) (SEQ ID NO: 7):

5'-CTCGAGGCCAGGG
3'-GAGCTCCGGTCCC-5'-label.

Restriction enzymes suitable for unilateral labeling are, for example, (a) restriction endonucleases with one or more recognition sequences of 5 nucleotides selected from AclWI, Alw26I, AlwI, AsuHPI, AvaII, BbvI, BcefI, BinI, BsbI, BscGI, Bse1I, BseNI, BsmAI, BsmFI, BspLU11III, BsrI, BsrSI, Bst71I, BstF5I, BstNI, CjeI, CjePI, EcoRII, FauI, FinI, FokI, HgaI, HphI, MboII, NciI, PleI, SfaNI, SimI, TauI, TfiI, TseI, Tsp45I, TspRI, or Vpa11AI;

(b) restriction endonucleases with at least one recognition sequence of 6 nucleotides selected from AccI, AflIII, AvaI, BanI, BanII, BmgI, BsaI, BsiEI, BsiHKAI, BsoBI, Bsp12861, DsaI, EcoO109I, GdiII, Hin4I, MmeI, SfcI, StyI, TatI, Tth111II, BglI, BbsI, BpiI, BpmI, BsaI, BsaMI, BseRI, BsmBI, BsmI, BspMI, Eam1104I, EarI, Eco31I, or Eco57I;

(c) restriction endonucleases with recognition sequences of 6 nucleotides which contain rarely-occurring nucleotide combinations such as, in particular, CG, selected from BsiI, BsmBI, Bst2BI, or Esp3I; and (d) restriction endonucleases with recognition sequences larger than 6 nucleotides selected from BaeI, PpuMI, RsrII, SanDI, SapI, SexAI, SfiI, I-CeuI, PI-PspI, I-PpoI, PI-TliI, or PI-SceI.

Hydrolysis with Restriction Enzymes

Each mixture is generally cut with at least one enzyme which cuts frequently. One of these enzymes in each mixture cuts the vector, in particular, in region B (enzyme E4, E5, or E6). It is also possible for the following different fragments to be produced by, for example, double hydrolyses with, for example, E3 and E5 (see FIGS. 3 and 4):

(1) a labeled E3-E5 fragment which contains the 3' end of the cDNA, (2) a labeled, short (<30 bp) E3-E5 fragment which contains vector sequences, and (3) several unlabelled E5-E5 fragments which may originate both from the vector and from the cDNA insert.

If the vector contains, for example, no cDNA insert or contains a cDNA insert which harbors no recognition sequence for the enzyme E5, then fragment 1 is generally at least 1000 base pairs in size because it contains region A (see FIG. 4).

Combination of the Reaction Products

In the case where the DNA has been labeled distinguishably in different mixtures, for example, by dyes differing in fluorescence behavior, the mixtures can generally be combined after inactivation of the restriction enzymes.

Purification of the Reaction Products

In the case where the DNA is labeled with radioactive isotopes or by dyes, all the resulting DNA fragments can be purified, for example, by ethanol precipitation.

If the analysis is to take place in a mass spectrometer, or if nonspecific labeling of DNA, for example, with DNA dyes such as ethidium bromide, is to take place subsequently, in general, the DNA fragments with the labeled ends are purified.

Analysis of the Fragment Lengths or Fragment Masses

Purification where appropriate is normally followed by determination of the fragment lengths and/or the fragment masses of the labeled DNA fragments. Fragment length can be determined, for example, after labeling with fluorescent dyes using an automatic DNA analysis system (for example ABI Prism™ 377). The methods for this are described in detail in the corresponding instructions by the manufacturers of these systems. The mixtures with the various enzymes can also be analyzed at the same time if the labeling has been carried out with three different dyes. In addition, a size marker labeled with a fourth dye is added in order to obtain an internal size standard. After fractionation and simultaneous detection in the DNA analysis system it is possible, by means of suitable software (for example ABI GeneScan) which compares the fluorescence signals from the mixtures with the signals of the marker, to determine and store the fragment size for all the signals. If the DNA has been radiolabeled or labeled with only one dye, in general, each mixture is analyzed individually, and an external size marker is generally also used. On analysis in a mass spectrometer (MALDI or ES, see, for example, Fu et al., 1998, Nature Biotech., 16, 381–4; U.S. Pat. Nos. 5,627,369; 5,716,825; 5,691,141), the mixtures are generally likewise analyzed individually.

Evaluation

The fragment lengths or masses determined above can subsequently be compared with a database. This database ought to have the lengths or masses of the restriction fragments from the 3' end of known cDNAs on file. This database can be constructed for known genes as follows.

Starting from the sequence, in general, the distance of the recognition sites for the enzymes E4, E5, and E6 from the 3' end of the cDNA (junction of the cDNA sequence with the poly-A tail) is found, and the length or the mass of this DNA fragment is calculated. Since the labeled cDNA fragments produced by the method described above still contain in addition a short, defined piece of poly-A tail and vector sequences (FIG. 1), the database entries are normally corrected. Accordingly, the length or mass of this additional sequence is added to the values in the database.

At least two, normally three, lists (one for each of the enzymes E3, E4, and E5) with fragment lengths or masses result each time the method is run through with a pool of cDNA clones. The entries in the lists are generally in the range of about 30–1000 base pairs. The number of entries in each of these lists corresponds to the number of cDNA clones, which have normally been combined, less the clones which contain only a short, incomplete, or no cDNA insert. Each list is then compared with the database. The cDNA pool may contain only the cDNAs of those genes for which there is a corresponding entry in each list. If the fragment length on file in the database does not appear in even one list, the cDNA of the gene was not present in the pool. If there is an entry corresponding to the fragment length of a gene in all the lists, the cDNA of the gene was present in the pool.

This comparison can be used to determine the known genes whose cDNAs were present in the pool. If no gene corresponding to an entry in one or more lists is found in the data bank, it may be assumed that a cDNA of an unknown gene was present in the pool. In such a case, the cDNAs of the pool are sequenced individually in order to identify the new gene. After identification of the new gene, data corresponding to that gene are included in the database. It is thus possible for the database to be continually supplemented and for virtually complete coverage of all the expressed genes to be achieved very quickly.

Normally about 20–200 cDNA clones are identified each time the method is run through. The exact number generally depends on various conditions. In the first place, the signals for each clone must be unambiguously detectable, that is, to be clearly distinguishable from the background. If the DNA is labeled by ligation of a fluorescence-labeled oligonucleotide, and if the analysis is carried out with an automatic DNA analysis system (ABI Prism™ 377, Applied Biosystems), it is normally possible to detect 200 signals unambiguously (see example below).

It should additionally be ensured that assignment to a gene is unambiguous, that is, a chance combination of fragment lengths must not lead to a false-positive identification of a cDNA in the pool. In order to preclude such a false-positive identification, the number of cDNAs in the pool which are analyzed at the same time should be limited. The maximum number of clones generally depends on the number of restriction enzymes used. If, for example, three different restriction enzymes are used and mammalian cells or tissue with about 20,000 different expressed genes are analyzed by means of fluorescence labeling and automatic DNA analysis systems, the maximum number of clones resulting is generally about 100.

If all 64 lanes of a gel are used in a conventional DNA analysis system, it is possible to identify 64×100=6,400 clones per gel run. With 10 gel runs a week, the resulting number of identified clones is 64,000. The mass spectrometer allows an even larger number of clones to be identified because of the greater accuracy of the analysis of fragment masses.

It is possible to determine from these data the relative frequency of the individual cDNAs in the cDNA library. Differentially expressed genes can be identified by comparing the relative frequencies in two or more cDNA libraries. The number of 64,000 clones generally allows accurate statistical confirmation of the frequencies for most genes. If it is also intended to compare very weakly expressed genes (1 to 5 copies per cell), it is normally necessary to analyze up to 300,000 clones.

The following figures and examples are intended to describe the invention in detail without restricting it.

DESCRIPTION OF THE PREFERRED EMBODIMENTS

Example 1

Description of the Vectors

A vector according to the invention was constructed by standard cloning methods (supra) as follows.

The vector pUC19 was cut with AatII and HindIII, and the fragment which is 2170 bp in size and contains the β-lactamase gene (ampicillin resistance) and the ColE1 origin of replication was isolated. The following double-stranded synthetic oligonucleotide was inserted between the AatII and HindIII cleavage sites (SEQ ID NOS: 8, 9):
5'-AGCTTGGCGCGCCGAATTCTATCTCGAGCGGCCG-CAGCTGAGATCGTACCCTATAGTGAGTCGTATTACGT-3'
3'-ACCGCGCGGCTTAAGATAGAGCTCGCCGGCGTCGACTCTAGCATGGGATATCACTCAGCATAA-5'

This resulted in the following arrangement of recognition sequences and elements:
HindIII-AscI-EcoRI-XhoI-NotI-AluI-DdeI-DpnI-RsaI-T7 promoter.

Two different vectors were generated starting from this construct.

Vector 1

Figure 1:
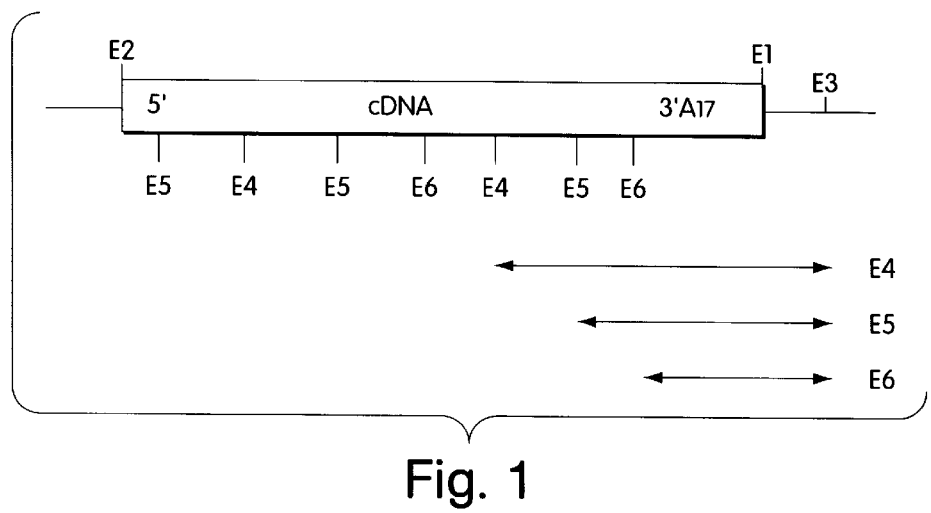
FIG. 1 is a diagram showing the identification of a cDNA clone on the basis of the characteristic distance of restriction cleavage sites (E4, E5, and E6) from the 3' end of the cDNA. The fragments of the cDNA produced by hydrolysis with the restriction enzymes E4, E5, or E6 and hydrolysis by the enzyme E3 comprise parts of the 3' end of the cDNA, a defined part of the poly-A tail, and short vector sequences (see double arrows).
Figure 2:
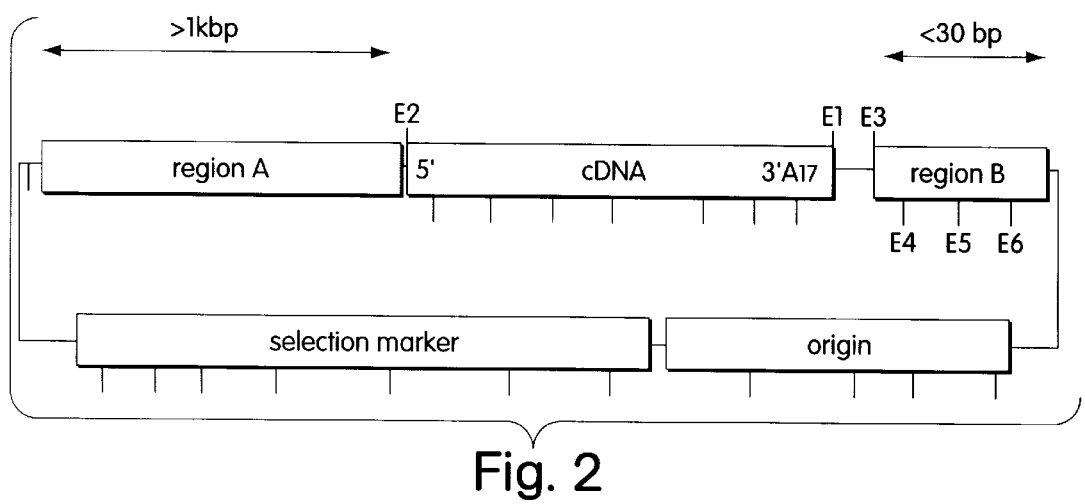
FIG. 2 is a diagram showing a cloning vector according to the invention (not to scale). E1 and E2 are recognition sequences of restriction enzymes, and the cDNA cloning site defined by E1 and E2 occurs only once in the vector. E3 is a recognition sequence for a restriction enzyme which cuts rarely, occurring only once in the vector. E4, E5, and E6 are recognition sequences for restriction enzymes which cut frequently. The lines under the boxes denote recognition sequences for the restriction enzymes E4, E5, or E6. The lines over the boxes denote recognition sequences for the restriction enzymes E1, E2, or E3. cDNA means a cloned cDNA with defined orientation, the 5' end of the cDNA being connected to region A and the 3' end being connected to region B. Region A means a nucleotide sequence which is larger than 1000 base pairs and has no recognition sequences for the restriction enzymes E1-E6. Region B means a nucleotide sequence which is smaller than 30 base pairs and contains recognition sites for the restriction enzymes E4, E5, and E6.
Figure 3:
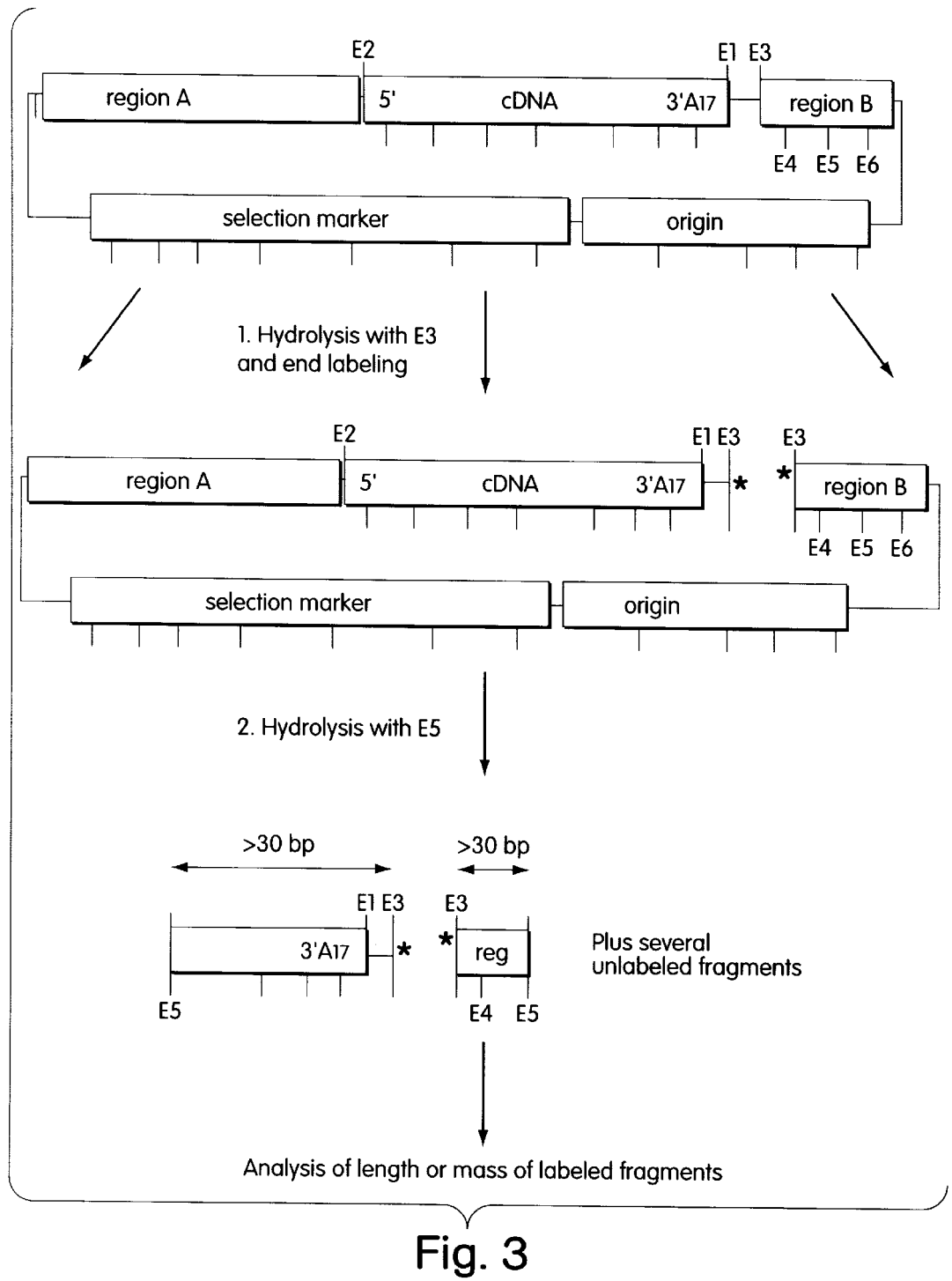
FIG. 3 is a diagram showing the hydrolysis and labeling of a vector according to the invention which contains a complete cDNA. The vector elements have been labeled as in FIG. 2. The full lines in the vector denote hydrolysis sites and the asterisks denote labels on the nucleic acid.
Figure 4:
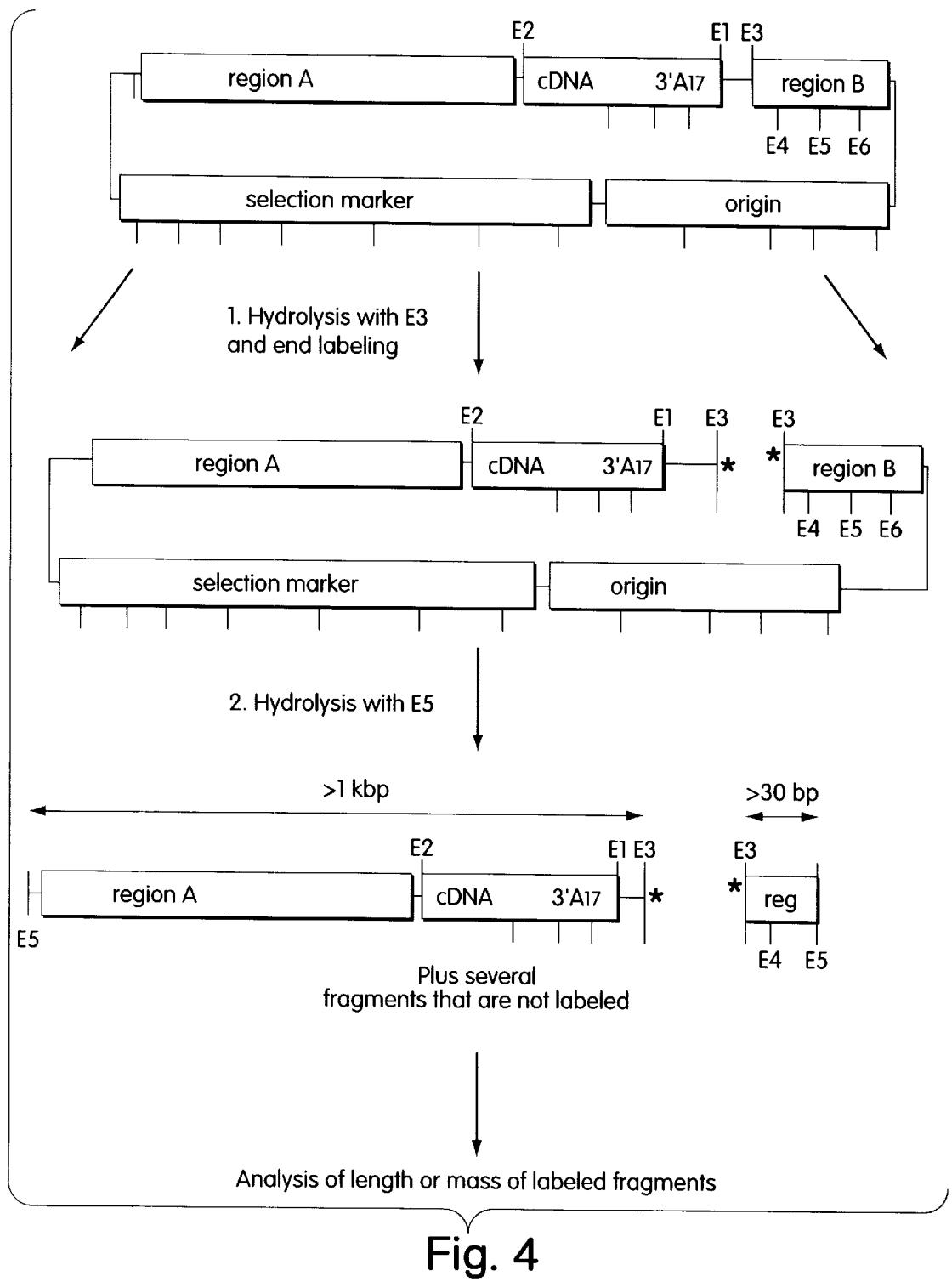
FIG. 4 is a diagram showing the hydrolysis and labeling of a vector according to the invention which contains an incomplete cDNA. The vector elements have been labeled as in FIGS. 2 and 3.
Figure 5:
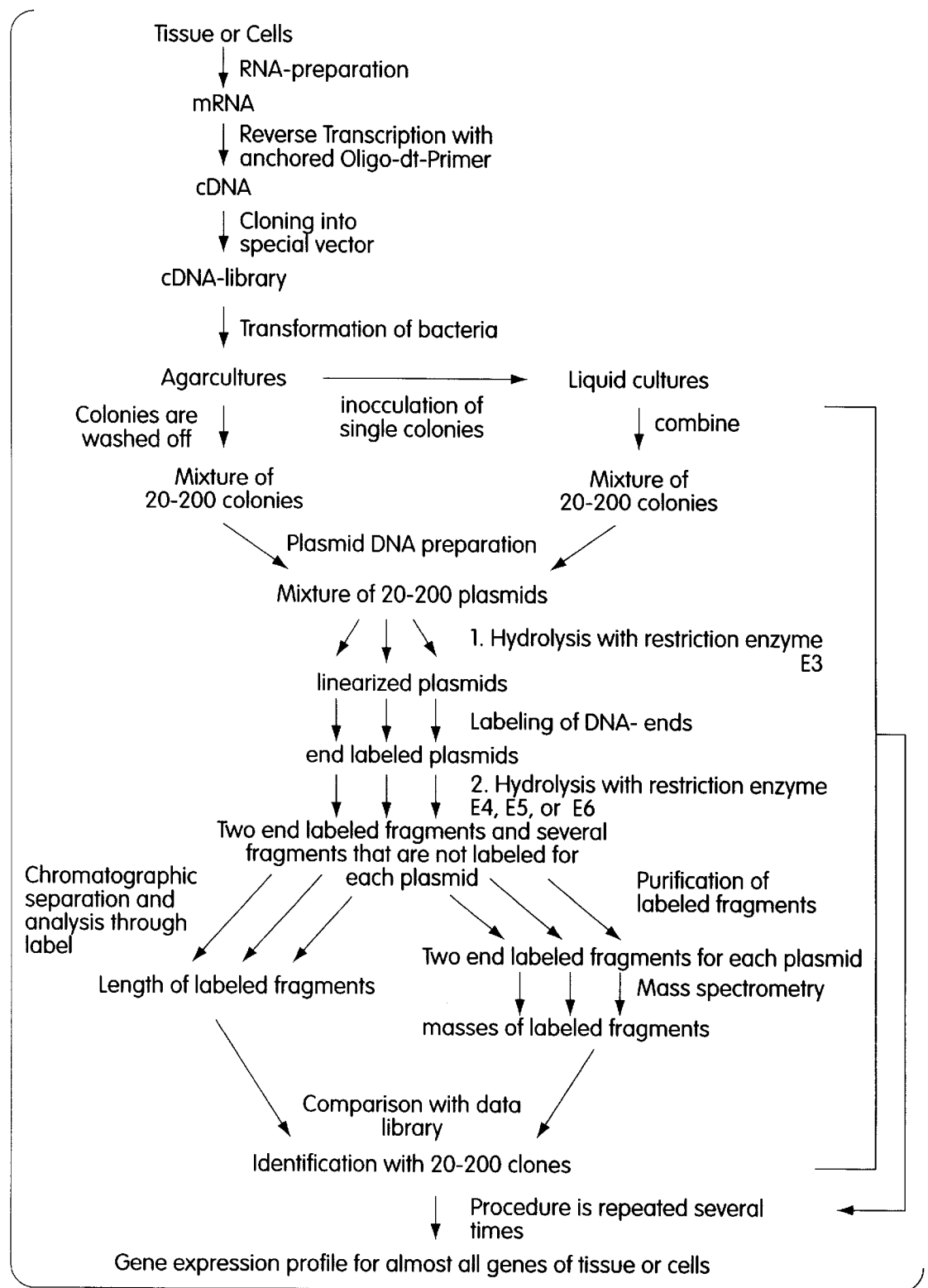
FIG. 5 is an outline of the method according to the invention. In this case, the steps from the mixing of the clones or cultures onwards are repeated several times until a sufficient number of clones have been identified. After preparation of the plasmid DNA, the method continues as described in three separate mixtures, the second hydrolysis being carried out with various restriction enzymes which cut frequently.

The DNA of bacteriophage λ was cut with DdeI and DpnI, and the fragment 901 bp in size was isolated. The DNA was blunt-ended by treatment with Klenow polymerase. A double-stranded phosphorylated AscI linker (5'-Pho-AGGCGCGCCT) (SEQ ID NO: 10) was ligated to the DNA ends of the fragment. Hydrolysis with AscI was carried out. The vector with the synthetic insert was likewise hydrolyzed with AscI, and the DNA fragment was integrated into the vector. The following sequence resulted at the integration site (SEQ ID NOS: 11, 12):
GGCGCGCCTTGAGT Insert GGGAAGGCGCGCC,
where the underlined region was derived from the 901 bp fragment. This resulted in the following assignments (compare FIG. 2):
E1: XhoI; E2: EcoRI; E3: NotI; E4: DdeI; E5: DpnI; E6: RsaI.

Cloning site of the cDNA: EcoRI-XhoI.

Region A: Region A extended from the EcoRI cleavage site to the first DdeI cleavage site which originated from the pUC19 portion. The total size of the region was 1558 bp, and it was composed of 634 bp which originated from the pUC19 portion, the 901 bp of the DNA fragment, and 23 bp of the synthetic insert. The region harbored no recognition sites for the enzymes XhoI, EcoRI, NotI, DdeI, DpnI, or RsaI.

Region B: Region B extended from the NotI to the RsaI cleavage site, additionally contained the recognition sequences for the enzymes DdeI and DpnI, and was 22 bp long.

Vector 2

A polymerase chain reaction with the primers (SEQ ID NOS: 13, 14):
5'-CCCCAAGCTTGTGAATATATCGAACAGTCAG-3' and 5'-CCGGCGCGCCTCCCGGTCTTTTCG-3' was carried out to amplify an 898 bp DNA fragment of bacteriophage λ, and the AscI and HindIII recognition sequences generated by the primers were hydrolyzed with the appropriate enzymes. The vector with the synthetic insert was likewise hydrolyzed with AscI and HindIII, and the isolated PCR fragment was integrated into the vector. The following sequence resulted at the integration site (SEQ ID NOS: 15, 16):
AAGCTTGTGAA Insert CGGGAGGCGCGCC
where the underlined region was derived from the 898 bp fragment. This resulted in the following assignments (compare FIG. 2)
E1: XhoI, E2: EcoRI, E3: Not1, E4: DdeI, E5: DpnI, E6: RsaI.

Cloning site of the cDNA: EcoRI-XhoI.

Region A: Region A extended from the EcoRI cleavage site to the first DdeI cleavage site which originated from the pUC19 portion. The total size of the region was 1546 bp, and it was composed of 634 bp which originated from the pUC19 portion, the 898 bp of the PCR fragment, and 14 bp of the synthetic insert. The region harbored no recognition sites for the enzymes XhoI, EcoRI, NotI, DdeI, DpnI, or RsaI.

Region B: Region B extended from the NotI to the RsaI cleavage site, additionally contained the recognition sequences for the enzymes DdeI and DpnI, and was 22 bp long.

Example 2

Preparation of a cDNA Library

The cDNA was synthesized using the "cDNA Synthesis Kit" (U.S. Pat. No. 5,681,726 Stratagene GmbH, Heidelberg, Germany #200401). The starting material comprised 5 μg of mRNA. For this purpose, the 5 μg of mRNA were denatured in 37.5 μl of water at 67° C. for 5 minutes, cooled on ice, and combined with 5 μl of 10×first strand synthesis buffer, 3 μl of methylated nucleotide mixture, 1 μl of RNase inhibitor and 3 μg of primer mixture. In place of the primer contained in the cDNA synthesis kit, a mixture of 12 primers was used (SEQ ID NO: 17):
5'-GAGAGAGAGAGAGAGAGAGAACTAGTCTCGAG TTTTTTTTTTTTTTVN-3'

The hybridization of the primer and the synthesis of the first strand took place after addition of 1.5 μl of MMLV reverse transcriptase (50 U/μl ) at 38° C. for 1 hour. The reaction mixture was then cooled on ice and, after addition of 20 μl of second strand synthesis buffer, 6 μl of nucleotide mixture, 116 μl of water, 2 μl of RNaseH, and 11 μl of DNA polymerase I, the second strand synthesis was carried out at 16° C. for 2.5 hours. The double-stranded cDNA was then blunt-ended after addition of 23 μl of nucleotide mixture and 2 μl of Pfu DNA polymerase at 72° C. for 30 minutes.

Phenol/chloroform extraction and ethanol precipitation were followed by ligation of the EcoRI adapter. For this purpose, the precipitated cDNA was dissolved in 9 μl of the EcoRI adapter solution, and the ligation was carried out after addition of 1 μl of the ligase buffer, 1 μl of 10 mM ATP, and 1 μl of T4 DNA ligase at 8° C. overnight. After thermal inactivation of the ligase (30 minutes at 70° C.), the DNA ends of the EcoRI adapter were phosphorylated after addition of 1 μl of ligase buffer, 2 μl of 10 μM ATP, 6 μl of water, and 1 μl of T4 polynucleotide kinase at 37° C. for 30 minutes. After thermal inactivation of the polynucleotide kinase (30 minutes, 70° C.), the cDNA was hydrolyzed after addition of 28 μl of XhoI buffer and 3 μl of XhoI at 37° C. for 1.5 hours.

After the hydrolysis with XhoI, the excess oligonucleotides and other impurities in the DNA were removed by agarose gel electrophoresis in low-melting agarose. The electrophoresis was followed by purification of the cDNA from the agarose by standard methods.

Integration into the vector described in Example 1 took place after hydrolysis of the vector with XhoI and EcoRI and purification of the vector fragment. A ratio of 100 ng of cDNA to 100 ng of vector in a volume of 5 μl was chosen for the ligase reaction with T4 DNA ligase.

After the ligation, the DNA was desalted by dialysis. Transformation took place by electroporation into competent XL1-Blue MRF' E. coli cells (Stratagene GmbH, Heidelberg, Germany, #200158) in accordance with the manufacturer's instructions.

Example 3

DNA Preparation. Hydrolysis, Labeling and Analysis of Clones

The cDNA library was plated out so that 55 to 75 colonies grew per selection plate (Petri dish with a diameter of 10 cm, LB agar medium with 100 μg/ml ampicillin (Sambrook et al., 1989 supra). After incubation at 37° C. for 24 hours, the colonies were rinsed off in 1 ml of TE buffer (10 mM Tris-HCl pH 8.0, 1 mM EDTA, pH 8.0) and pelleted in a microcentrifuge. The bacteria were disrupted by alkaline lysis, and the plasmid DNA was isolated by standard methods and taken up in 60 μl of TE buffer.

The first hydrolysis with E3 (NotI) and the end-labeling took place in a coupled reaction. The labeling took place by ligating a double-stranded unphosphorylated oligonucleotide. The shorter oligonucleotide carried at its 5' end a dye (either FAM (5-carboxyfluorescein), TAMRA (N,N,N',N'-tetramethyl-6carboxyrhodamine), or JOE (2',7'-dimethoxy-4', 5'-dichloro-6-carboxyfluorescein). The longer oligonucleotide was complementary to the shorter and hybridized in such a way that its 5' end formed an overhang which is complementary to the 5' overhang after hydrolysis with the restriction enzyme NotI. In the ligase reaction there was covalent linkage of the 3' end of the labeled oligonucleotide to the 5' end of the NotI cleavage site. The chosen oligonucleotide sequence prevented renewed hydrolysis with NotI from being possible after the ligation, because the NotI recognition sequence was not regenerated.

The sequences of the oligonucleotides were as follows (SEQ ID NO: 18):
Label—5'-CAGGAGATGCTGTTCGT-3'
3'- TCCTCTACGACAAGCACCGG-5'

The plasmid DNA was distributed in 3 mixtures, each containing 10 μl. The reaction was started by adding 15 μl of reaction mixture. The final concentrations in the reaction mixtures were as follows: 20 mM Tris-acetate, pH 7.9 at 25° C.; 10 mM magnesium acetate; 50 mM potassium acetate; 0.1 μg/μl acetylated BSA; 6 mM DTT; 1 mM ATP; 0.16 μM of the double-stranded oligonucleotide; 0.2 units/μl NotI; and 0.04 units/μl T4 DNA ligase (Weiss units). Incubation took place at 37° C. for 16 hours. After the hydrolysis and labeling, the enzymes were thermally inactivated at 65° C. for 15 minutes. The second hydrolysis with the restriction enzymes E4 (DdeI), E5 (DpnI), or E6 (RsaI) took place by adding 20 μl of the following reaction mixture: 20 mM Tris-acetate, pH7.9 at 25° C.; 10 mM magnesium acetate; 50 mM potassium acetate; 0.1 μg/μl acetylated BSA; 0.1 units/μl of the appropriate enzyme. The mixture which had been labeled with the FAM-labeled oligonucleotide was hydrolyzed with DdeI. In the case of labeling with TAMRA, the hydrolysis was carried out with DpnI, and in the case of labeling with JOE the hydrolysis was carried out with RsaI.

The reaction was incubated at 37° C. for 3 hours. The restriction enzymes were then inactivated by incubation at 95° C. for 5 minutes and the three mixtures were combined. The DNA was precipitated after addition of 15 μl of 3 M sodium acetate and 375 μl of ethanol at 20° C. for 30 minutes. After pelleting in a microcentrifuge, the pellet was washed with 70% ethanol and dissolved in 2 μl of loading buffer (80% formamide, 5 mM EDTA, 2 mg/ml dextran blue, 10% by volume GeneScan-2500 Rox size marker, Applied Biosystems Product No. 401100). The mixtures were denatured at 95° C. for 3 minutes and immediately cooled on ice.

The fragments were fractionated in an automatic DNA analysis system (ABI Prism™ 377, Applied Biosystems) on a denaturing 4% polyacrylamide gel, which was 36 cm long and 0.2 mm thick, in accordance with the manufacturer's instructions (Applied Biosystems).

The fragment lengths were evaluated by comparison with the size marker (GeneScan-2500 Rox) using appropriate software (GeneScan, Applied Biosystems). It was possible to determine the sizes of up to 70 fragments in all three mixtures, depending on the original number of clones. The standard deviation of the analysis was less than 0.1 base pair for a fragment length up to 500 base pairs, and less than 1.0 base pair above 500 base pairs.

Example 4

Comparison of Expression of the Gene SPR1a in Skin and Liver

The gene SPR1a is known to be expressed specifically and strongly in mouse skin (Kartasova et al., 1996, J. Invest. Dermatol. 106, 294–304). Clones of this gene therefore occur frequently in skin cDNA libraries and distinctly more rarely or not at all in cDNA libraries from other tissues (for example, liver). This gene was therefore chosen for the validation of the method.

mRNAs were isolated from mouse skin and liver tissue, and two cDNA pools were prepared (see Example 2). These were cloned into Vector 2 described in Example 1, and two cDNA libraries were produced. About 5000 clones from each of these libraries were analyzed as described in Example 3.

The lengths of the 3' cDNA fragments produced by hydrolysis with DdeI (77 bp), DpnI (273 bp), and RsaI (703 bp) were determined from the published sequence of SPR1a (Kartosova et al., supra). Since the analyzed fragments of the cDNAs still contained, in addition, defined sequences of the poly-A tail of the vector and of the labeling oligonucleotide (together, 44 bp), the fragment lengths were corrected correspondingly. The fragment lengths calculated in this way for DdeI (121 bp), DpnI (317 bp), and RsaI (747 bp) were compared with the data from the analyses. Account was taken of the fact that DNA fragments show sequence-dependent and reproducible differences in the migration rate in denaturing polyacrylamide gels, so that the fragment lengths determined by comparison with a size marker may differ by about 1% from the actual fragment lengths (Frank and Köster, 1979, Nucleic Acids Res. 6, 2069–87). Clones with fragment lengths comparable with the published sequence of SPR1a (DdeI: 120.59+0.04 bp, DpnI: 319.89+0.04 bp, RsaI: 750.80+0.30bp) occurred 8 times in the analysis of the skin cDNA library but not once in the analysis of the liver cDNA library. Isolation and sequencing of one of these clones confirmed that these clones contained the cDNA from SPR1a. It can be inferred from these data that about 0.16% (8/5000) of the mRNAs in the skin originated from the SPR1a gene, while the frequency in the liver was less than 0.02%, which is consistent with the published data mentioned above.

It was possible to obtain comparable data for other genes. Thus, for example, the fragment pattern of serum albumin was found 27 times in the analysis of the liver cDNA library but not in the analysis of the skin cDNA library. The frequency (about 0.5%) of serum albumin mRNA found in this way in the mouse liver was consistent with the published data on the expression of serum albumin (Sellem et al., 1984, Dev. Biol. 102,51–60).

What is claimed is:

1. A cloning vector comprising:
   (a) a cloning site which permits the cloning of a nucleic acid in a defined orientation;
   (b) at least one cleavage site located adjacent to said cloning site, said cleavage site being rarely-occurring in nucleic acids, wherein said cleavage site is recognized by a restriction endonuclease selected from AscI, BaeI, FseI, NotI, PmeI, PpuMI, RsrII, SanDI, SapI, SexAI, SfiI, SgfI, SgrAI, SrfI, Sse8387I, SwaI, I-CeuI, PI-PspI, I-PpoI, PI-TliI, and PI-SceI, or is recognized by a restriction endonuclease with a recognition sequence of not less than 8 nucleotides that includes a CG combination;
   (c) a short region having several different cleavage sites which are frequently-occurring in nucleic acids, said short region being positioned on the side of said cleavage site (b) opposite to said cloning site, wherein said short region is shorter than about 100 nucleotides; and
   (d) a long region located on the side of said cloning site opposite to said cleavage site (b), wherein said long region and the region between said cloning site and said cleavage site (b) contain neither said cloning site nor at least three of said frequently-occurring cleavage sites, wherein said long region is longer than at least 500 nucleotides.

2. The cloning vector according to claim 1, characterized in that said cloning site contains two different cleavage sites.

3. The cloning vector according to claim 1, characterized in that said frequently-occurring cleavage sites, independently of one another, are recognized by restriction endonucleases having recognition sequences of not more than 4 nucleotides.

4. The cloning vector according to claim 3, characterized in that each of said frequently-occurring cleavage sites is recognized independently by a restriction endonuclease selected from AciI, AluI, BfaI, BsaJI, Bs1I, BscFI, BssKI, BstUI, Cac8I, CfoI, Csp6I, CviJI, DdeI, DpnI, DpnII, FmuI, Fnu4HI, HaeIII, HhaI, HinfI, HinPI, HpaII, MaeII, MaeIII, MboI, MnlI, MseI, MspI, MwoI, NlaIII, NlaIV, RsaI, Sau3AI, Sau96I, ScrFI, TaiI, TaqI, Tsp4CI, or Tsp509I.

5. The cloning vector according to claim 1, characterized in that said cloning site is selected from a cleavage site which is recognized by restriction endonucleases with a recognition sequence of not less than 5 nucleotides.

6. The cloning vector according to claim 1, characterized in that said cloning site is selected from a cleavage site which is recognized by restriction endonucleases with a recognition sequence of not less than 6 nucleotides.

7. The cloning vector according to claim 1, characterized in that said cloning site is selected from a cleavage site which is recognized by restriction endonucleases with a recognition sequence of not less than 8 nucleotides.

8. The cloning vector according to claim 6, characterized in that said cloning site is recognized by a restriction endonuclease selected from AClWI, Alw26I, AlwI, AsuHPI, AvaII, BbvI, BccI, BcefI, BinI, BsbI, BscGI, Bse1I, BseNI, BsmAI, BsmFI, BspLU11III, BsrI, BsrSI, Bst71I, BstF5I, BstNI, CjeI, CjePI, EcoRII, FauI, FinI, FokI, HgaI, HphI, MboII, NciI, PleI, SfaNI, SimI, TauI, TfiI, TseI, Tsp45I, TspRI, or Vpa11AI.

9. The cloning vector according to claim 6, characterized in that said cloning site is recognized by a restriction endonuclease selected from AccI, AflIII, ApoI, AvaI, AvaII, BanI, BanII, BmgI, BsaI, BsaHI, BsaWI, BsiEI, BsiHKAI, BsoBI, Bsp1286I, BsrFI, BstYI, DsaI, EaeI, EcoO109I, GdiII, HaeI, HaeII, Hin4I, HincII, MmeI, Ms1I, MspA1I, NspI, SfcI, StyI, TatI, Tth111II, AatI, Acc131I, Acc65I, AcINI, AflII, Alw44I, ApaI, ApaLI, AseI, Asp718I, AvrII, Ba1I, BamHI, BbuI, BbsI, Bc1I, BfrI, Bg1I, Bg1II, BlnI, BpiI, BpmI, BsaI, BsaMI, BseRI, BsmBI, BsmI, Bsp120I, Bsp1407I, Bsp191I, BspHI, BspLU11I, BspMI, BspTI, BsrGI, Bst1107I, Bst98I, DraI, Eam1104I, EarI, Ecl136II, Eco147I, Eco255I, Eco57I, EcoNI, EcoRI, EcoRV, EcoT22I, HindIII, HpaI, KpnI, MfeI, MscI, NcoI, NdeI, NheI, NsiI, PstI, PvuII, SacI, ScaI, SpeI, SphI, SspI, SstI, StuI, or XbaI.

10. The cloning vector according to claim 6, characterized in that said cloning site is recognized by a restriction endonuclease with a recognition sequence which contains a rare nucleotide combination.

11. The cloning vector according to claim 10, characterized in that said rare nucleotide combination is CG.

12. The cloning vector according to claim 10, characterized in that said cloning site is recognized by one of the restriction endonuclease selected from AatII, BbeI, BsiI, BsiWI, BsmBI, BspDI, BsrBI, BssHII, Bst2BI, BstBI, ClaI, EagI, EciI, Eco47III, EheI, Esp3I, FspI, KasI, MluI, NarI, NruI, Pfl1108I, PmlI, Psp1406I, PvuI, SacII, SalI, SnaBI, or XhoI.

13. The cloning vector according to claim 6, characterized in that said cloning site is recognized by a restriction endonuclease selected from AscI, BaeI, FseI, NotI, PacI, PmeI, PpuMI, RsrII, SanDI, SapI, SexAI, SfiI, SgfI, SgrAI, SrfI, Sse8387I, SwaI, I-CeuI, PI-PspI, I-PpoI, PI-TliI, or PI-SceI.

14. The cloning vector according to claim 1, characterized in that said long region is longer than the fragments obtainable by cutting with restriction endonucleases which recognize frequently-occurring cleavage sites.

15. The cloning vector according to claim 1, wherein said long region is longer than about 1000 nucleotides.

16. The cloning vector according to claim 1, characterized in that said short region is smaller than the length of the nucleic acid which extends from cleavage site (b) to the first possible cleavage site in the nucleic acid to be inserted into said cloning vector.

17. The cloning vector according to claim 16, characterized in that said frequently-occurring cleavage site occurs at the start of the poly(A) tail of a cDNA to be inserted into said cloning site of said cloning vector.

18. The cloning vector according to claim 1, wherein said short region is shorter than about 30 nucleotides.

19. A method for the preparation of a cloning vector according to claim 1, said method comprising combining the individual components of the vector.

20. A cloning vector comprising:
(a) a cloning site which permits the cloning of a nucleic acid in a defined orientation;
(b) at least one cleavage site located adjacent to said cloning site, said cleavage site being rarely-occurring in nucleic acids, wherein said cleavage site is recognized by a restriction endonuclease selected from SfiI, BglI, BbsI, BsaI, and BspMI; and
(c) a long region located on the side of said cloning site opposite to said cleavage site (b), wherein said long region and the region between said cloning site and said cleavage site (b) contain neither said cloning site nor at least three different frequently-occurring cleavage sites, said frequently-occurring cleavage sites comprising DdeI, DpnI, and RsaI, and wherein said long region is longer than at least 500 nucleotides.

21. The cloning vector of claim 20, wherein said cloning vector further comprises a short region, said short region having several different cleavage sites which are frequently-occurring in nucleic acids but which do not occur in said long region, said short region being positioned on the side of said cleavage site (b) opposite to said cloning site, wherein said short region is shorter than about 100 nucleotides.

* * * * *

UNITED STATES PATENT AND TRADEMARK OFFICE
CERTIFICATE OF CORRECTION

PATENT NO.   : 6,303,308 B1  
DATED        : October 16, 2001  
INVENTOR(S)  : Jörn-Peter Halle, Johannes Regenbogen and Andreas Goppelt It is certified that error appears in the above-identified patent and that said Letters Patent is hereby corrected as shown below:

<u>Title page,</u>  
Item [56], References Cited, OTHER PUBLICATIONS,  
New England Biolabs Catalog reference, change ""pnEB 193","  to  
-- "pnEB 193," --;

<u>Column 10,</u>  
Line 36, change "sfll" to -- sfil --;  
Line 43, change "3'" to -- 3'→ --;

<u>Column 16,</u>  
Line 39, change "pH7.9" to -- pH 7.9 --;

<u>Column 18,</u>  
Line 9, change " Köster, " to -- Köster --;

<u>Column 23,</u>  
Line 34, change "PI-Scel" to -- PI-SceI --;

<u>Column 24,</u>  
Line 34, change ?claim 6" to -- claim 5 --;  
Line 48, change "Acc131I" to -- Acc113I --;  
Line 52, change "Bsp191I" to -- Bsp19I --;

<u>Column 25,</u>  
Line 25, change "cDNA to be inserted" to -- cDNA inserted --.

Signed and Sealed this

Seventeenth Day of September, 2002

*Attest:*

JAMES E. ROGAN  
*Attesting Officer*    *Director of the United States Patent and Trademark Office*

SEQUENCE LISTING

<160> NUMBER OF SEQ ID NOS: 18

<210> SEQ ID NO 1
<211> LENGTH: 33
<212> TYPE: DNA
<213> ORGANISM: Artificial Sequence
<220> FEATURE:
<223> OTHER INFORMATION: DNA primer

<400> SEQUENCE: 1
gagagagaga ctcgagtttt tttttttttt ttt                33

<210> SEQ ID NO 2
<211> LENGTH: 13
<212> TYPE: DNA
<213> ORGANISM: Artificial Sequence
<220> FEATURE:
<223> OTHER INFORMATION: restriction enzyme cleavage site

<400> SEQUENCE: 2
ggccagggtg gcc                13

<210> SEQ ID NO 3
<211> LENGTH: 24
<212> TYPE: DNA
<213> ORGANISM: Artificial Sequence
<220> FEATURE:
<223> OTHER INFORMATION: restriction enzyme cleavage site

<400> SEQUENCE: 3
ctcgaggcca gggtggccga tcga                24

<210> SEQ ID NO 4

```
<211> LENGTH: 13
<212> TYPE: DNA
<213> ORGANISM: Artificial Sequence
<220> FEATURE:
<223> OTHER INFORMATION: restriction enzyme cleavage site

<400> SEQUENCE: 4
ctcgaggcca ggg                                                          13

<210> SEQ ID NO 5
<211> LENGTH: 14
<212> TYPE: DNA
<213> ORGANISM: Artificial Sequence
<220> FEATURE:
<223> OTHER INFORMATION: restriction enzyme cleavage site

<400> SEQUENCE: 5
tcgatcggcc accc                                                         14

<210> SEQ ID NO 6
<211> LENGTH: 13
<212> TYPE: DNA
<213> ORGANISM: Artificial Sequence
<220> FEATURE:
<223> OTHER INFORMATION: Oligonucleotide

<400> SEQUENCE: 6
ccctggcctc gag                                                          13

<210> SEQ ID NO 7
<211> LENGTH: 13
<212> TYPE: DNA
<213> ORGANISM: Artificial Sequence
<220> FEATURE:
<223> OTHER INFORMATION: DNA end

<400> SEQUENCE: 7
ccctggcctc gag                                                          13

<210> SEQ ID NO 8
<211> LENGTH: 71
<212> TYPE: DNA
<213> ORGANISM: Artificial Sequence
<220> FEATURE:
<223> OTHER INFORMATION: DNA fragment

<400> SEQUENCE: 8
agcttggcgc gccgaattct atctcgagcg gccgcagctg agatcgtacc ctatagtgag        60
tcgtattacg t                                                            71

<210> SEQ ID NO 9
<211> LENGTH: 63
<212> TYPE: DNA
<213> ORGANISM: Artificial Sequence
<220> FEATURE:
<223> OTHER INFORMATION: DNA fragment

<400> SEQUENCE: 9
aatacgactc actatagggt acgatctcag ctgcggccgc tcgagataga attcggcgcg        60
cca                                                                     63

<210> SEQ ID NO 10
<211> LENGTH: 10
<212> TYPE: DNA
<213> ORGANISM: Artificial Sequence
```

```
<220> FEATURE:
<223> OTHER INFORMATION: DNA linker

<400> SEQUENCE: 10
aggcgcgcct                                                              10

<210> SEQ ID NO 11
<211> LENGTH: 14
<212> TYPE: DNA
<213> ORGANISM: Artificial Sequence
<220> FEATURE:
<223> OTHER INFORMATION: DNA integration site

<400> SEQUENCE: 11
ggcgcgcctt gagt                                                         14

<210> SEQ ID NO 12
<211> LENGTH: 13
<212> TYPE: DNA
<213> ORGANISM: Artificial Sequence
<220> FEATURE:
<223> OTHER INFORMATION: DNA integration site

<400> SEQUENCE: 12
gggaaggcgc gcc                                                          13

<210> SEQ ID NO 13
<211> LENGTH: 31
<212> TYPE: DNA
<213> ORGANISM: Artificial Sequence
<220> FEATURE:
<223> OTHER INFORMATION: DNA primer

<400> SEQUENCE: 13
ccccaagctt gtgaatatat cgaacagtca g                                      31

<210> SEQ ID NO 14
<211> LENGTH: 24
<212> TYPE: DNA
<213> ORGANISM: Artificial Sequence
<220> FEATURE:
<223> OTHER INFORMATION: DNA primer

<400> SEQUENCE: 14
ccggcgcgcc tcccggtctt ttcg                                              24

<210> SEQ ID NO 15
<211> LENGTH: 11
<212> TYPE: DNA
<213> ORGANISM: Artificial Sequence
<220> FEATURE:
<223> OTHER INFORMATION: DNA integration site

<400> SEQUENCE: 15
aagcttgtga a                                                            11

<210> SEQ ID NO 16
<211> LENGTH: 13
<212> TYPE: DNA
<213> ORGANISM: Artificial Sequence
<220> FEATURE:
<223> OTHER INFORMATION: DNA integration site

<400> SEQUENCE: 16
cgggaggcgc gcc                                                          13
```

```
<210> SEQ ID NO 17
<211> LENGTH: 48
<212> TYPE: DNA
<213> ORGANISM: Artificial Sequence
<220> FEATURE:
<223> OTHER INFORMATION: DNA primer

<400> SEQUENCE: 17
gagagagaga gagagagaga actagtctcg agtttttttt tttttttt                        48

<210> SEQ ID NO 18
<211> LENGTH: 17
<212> TYPE: DNA
<213> ORGANISM: Artificial Sequence
<220> FEATURE:
<223> OTHER INFORMATION: DNA oligonucleotide

<400> SEQUENCE: 18
caggagatgc tgttcgt                                                          17
```